(12) United States Patent
Tamarindo

(10) Patent No.: US 11,383,868 B2
(45) Date of Patent: Jul. 12, 2022

(54) SYSTEM FOR HANDLING THE STERILISATION OF FLEXIBLE POUCHES

(71) Applicant: GUALA PACK S.p.A., Castellazzo Bormida (IT)

(72) Inventor: Stefano Tamarindo, Castellazzo Bormida (IT)

(73) Assignee: GUALA PACK S.p.A., Castellazzo Bormida (IT)

( * ) Notice: Subject to any disclaimer, the term of this patent is extended or adjusted under 35 U.S.C. 154(b) by 117 days.

(21) Appl. No.: 16/089,225

(22) PCT Filed: Mar. 28, 2017

(86) PCT No.: PCT/IB2017/051768
§ 371 (c)(1),
(2) Date: Sep. 27, 2018

(87) PCT Pub. No.: WO2017/168322
PCT Pub. Date: Oct. 5, 2017

(65) Prior Publication Data
US 2019/0106233 A1 Apr. 11, 2019

(30) Foreign Application Priority Data
Mar. 30, 2016 (IT) .................. 102016000032367

(51) Int. Cl.
*B65B 55/08* (2006.01)
*B65B 55/04* (2006.01)
(Continued)

(52) U.S. Cl.
CPC .............. *B65B 55/08* (2013.01); *A61L 2/081* (2013.01); *A61L 2/087* (2013.01); *A61L 2/26* (2013.01);
(Continued)

(58) Field of Classification Search
CPC ....... B65B 55/027; B65B 55/04; B65B 55/08; B65B 55/10; B65B 55/02; B65B 55/12;
(Continued)

(56) References Cited

U.S. PATENT DOCUMENTS 4,390,104 A 6/1983 Cummings
4,445,550 A 5/1984 Davis et al.
(Continued)

FOREIGN PATENT DOCUMENTS

EP 2611704 A1 7/2013
EP 2701751 3/2014
(Continued)

OTHER PUBLICATIONS

Italian Search Report dated Dec. 6, 2016, ITUA dated Jun. 21, 2016, Munich, 10 pages.
(Continued)

*Primary Examiner* — Chinyere J Rushing-Tucker
(74) *Attorney, Agent, or Firm* — Thomas | Horstemeyer, LLP

(57) ABSTRACT

A system of managing the sterilisation of empty flexible pouches (1) provides applying sacrificial closures (200) to the empty pouches, loading the empty provisional closed pouches to be sterilised on a transport device (300) for the collective transportation, performing the sterilisation of the transport device (300) carrying the empty provisional closed pouches, and finally separating, in a sterile chamber, the sacrificial closures (200) from the pouches, filling and applying a tamper-proof cap (100).

12 Claims, 5 Drawing Sheets

(51) Int. Cl.
    *A61L 2/08*     (2006.01)
    *A61L 2/26*     (2006.01)
    *B65B 3/02*     (2006.01)
    *B65B 3/04*     (2006.01)
    *B65B 7/02*     (2006.01)
    *B65B 43/42*     (2006.01)
    *B65B 55/02*     (2006.01)
    *B65B 61/18*     (2006.01)

(52) U.S. Cl.
    CPC ............... *B65B 3/02* (2013.01); *B65B 3/045* (2013.01); *B65B 7/02* (2013.01); *B65B 43/42* (2013.01); *B65B 55/027* (2013.01); *B65B 55/04* (2013.01); *B65B 61/186* (2013.01); *A61L 2202/23* (2013.01)

(58) Field of Classification Search
    CPC .. B65B 3/02; B65B 3/045; B65B 3/04; B65B 7/02; B65B 43/42; B65B 61/186; B65B 61/20; B65B 25/001; A61L 2/081; A61L 2/087; A61L 2/26; A61L 2202/23; B65D 75/5883; B65D 75/58
    USPC ........ 53/426, 133.1, 133.2, 133.4, 412, 468, 53/469
    See application file for complete search history.

(56) References Cited

U.S. PATENT DOCUMENTS

| | | | |
|---|---|---|---|
| 5,860,461 A | 1/1999 | Helmut | |
| 6,053,360 A | 4/2000 | Rutter | |
| 6,925,780 B1 * | 8/2005 | Anderson | B65B 55/022 53/109 |
| 8,490,662 B2 * | 7/2013 | Murray | B65B 43/42 141/372 |
| 9,340,309 B2 | 5/2016 | Nakagawa et al. | |
| 9,809,370 B2 | 11/2017 | Bellmore et al. | |
| 2006/0086065 A1 * | 4/2006 | Tomalesky | B65B 7/2835 53/425 |
| 2010/0170591 A1 | 7/2010 | Murray | |
| 2011/0016829 A1 * | 1/2011 | Drenguis | A61L 2/087 53/426 |
| 2011/0017343 A1 | 1/2011 | Murray | |
| 2012/0279177 A1 * | 11/2012 | Macquet | B65B 7/2835 53/426 |
| 2016/0046427 A1 * | 2/2016 | Bellmore | B65D 75/5877 383/42 |
| 2017/0081064 A1 | 3/2017 | van der Meijden et al. | |

FOREIGN PATENT DOCUMENTS

| | | | | |
|---|---|---|---|---|
| EP | 2701979 | | 3/2014 | |
| JP | H05170252 A | | 7/1993 | |
| JP | 2001122225 A | | 5/2001 | |
| JP | 2002321715 A | | 11/2002 | |
| JP | 2003237742 A | | 8/2003 | |
| JP | 2011001130 A | | 1/2011 | |
| JP | 2013133106 A | | 7/2013 | |
| JP | 2016008055 A | | 1/2016 | |
| NL | 2015473 B1 | * | 9/2015 | |
| WO | WO 2012055459 A1 | * | 3/2012 | |
| WO | 2012055459 A1 | | 5/2012 | |
| WO | WO-2012055459 A1 | * | 5/2012 | ........... B65B 61/186 |
| WO | 2014171834 A2 | | 10/2014 | |
| WO | 2017001947 | | 1/2017 | |

OTHER PUBLICATIONS

Non Final Office Action issue by the USPTO for U.S. Appl. No. 15/417,446, dated Oct. 2, 2019.
Final Office Action issue by the USPTO for U.S. Appl. No. 15/417,446, dated Apr. 30, 2020.
Advisory Office Action issue by the USPTO for U.S. Appl. No. 15/417,446, dated Jul. 24, 2020.
International Search Report and Written Opinion for PCT/IB2017/051768 dated Jul. 24, 2017.
International Preliminary Report on Patentability for PCT/IB2017/051768 dated May 3, 2018.
Reply to Written Opinion of the International Preliminary Examining Authority filed in PCT/IB2017/051768 dated Mar. 19, 2018.
Third Party Observation filed in PCT/IB2017/051768 filed on Feb. 15, 2018.
Communication issued by the European Patent Office for application EP17719339.8, dated Dec. 9, 2020.
Office Action issued for Japanese application 2017-064519, dated Feb. 24, 2021.
Office Action issued for Japanese application 2017-064519, dated Jul. 13, 2021.

* cited by examiner

SYSTEM FOR HANDLING THE STERILISATION OF FLEXIBLE POUCHES

CROSS-REFERENCE TO RELATED APPLICATION

This application is the 35 U.S.C. § 371 national stage application of PCT Application No. PCT/IB2017/051768, filed Mar. 28, 2017, where the PCT claims the priority to and benefit of Italian Patent Application No. 102016000032367, filed Mar. 30, 2016, both of which are herein incorporated by reference in their entireties.

The object of the present invention is a method and an apparatus for preparing flexible pouches for sterilisation. Such pouches generally are used for containing food products such a fruit juices, yoghurt, fruit purée, creams, honey and the like, or medicines and the like.

In the food sector, the sterilisation of such a type of pouch is enormously important for avoiding contaminations and the proper conservation of the food therein contained.

Sometimes, a chemical sterilisation is performed during which the pouch is washed with disinfecting agents, e.g. hydrogen peroxide, and then is dried before being sent to the successive filling operations.

However, chemical sterilisation has certain disadvantages such as for example, the presence of residues of the disinfecting agent in the dry container or the presence of non-disinfected areas due to complex or irregular geometries of the pouch. Such a disadvantage is particularly felt in the field of pouches.

Instead, sterilisation by ionising radiation, such as gamma rays or electron beams, is very widespread in the sector. For example, Patents EP 2701751 and EP 2701979 relating to electron beam sterilisation systems, to the Applicant.

Usually, the performance of sterilisation by ionising radiation is performed in specialized centres where the manufacturer of the pouches sends the pouches to be treated; once the sterilisation has been performed, the sterile pouches are sent to the filler and the applier of the closure using contrivances which allow maintaining the sterility condition inside the pouch.

Such logistics obviously imply significant transport costs between the sites and significant complexity in managing the pouches within the sites themselves.

To obviate such a drawback, the Applicant has already conceived a system for managing the sterilisation of flexible pouches, disclosed for example, in International Application PCT/IB2016/051108.

According to the aforesaid management system, the use is provided of a plurality of sacrificial closures reversibly applied to the outlet of the spout of empty pouches, which are separated from the spout in a sterile chamber, after the empty provisional closed pouches have been sterilised and immediately prior to filling the pouch.

It is the object of the present invention to provide a method and an apparatus for preparing for the sterilisation the empty flexible pouches which use further types of closures suitable for optimizing the process which transforms the empty pouch to be sterilised into the sterilised and full pouch.

Such an object is achieved by the methods, assemblies and transport devices according to the following claims.

The features and advantages of the present invention will become apparent from the following description, given by way of a non-limiting example, according to the accompanying drawings, in which.

Figure 1:
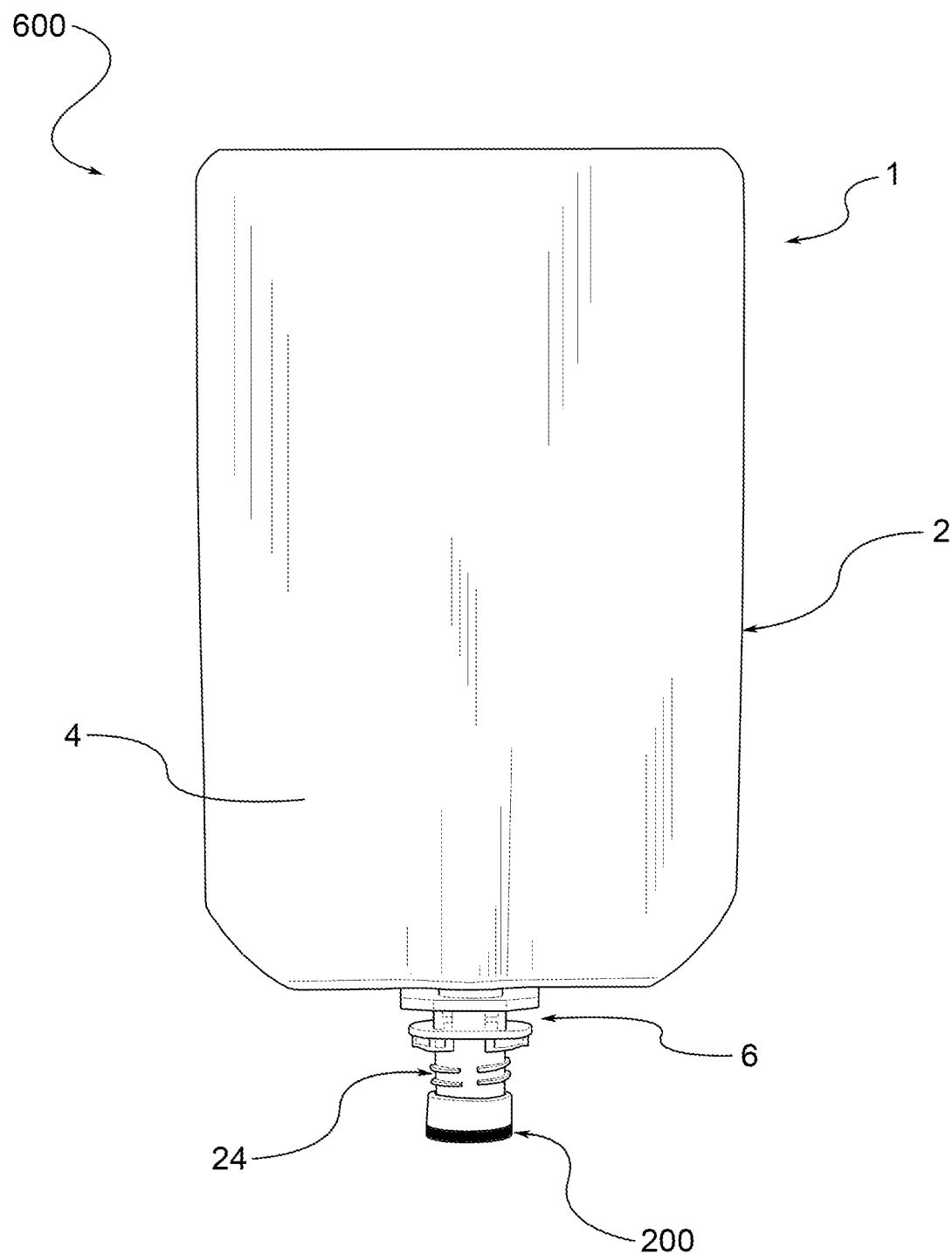
FIG. 1 shows an empty pouch provided with a sacrificial closure.

With reference to the accompanying drawings, numeral 1 indicates a flexible pouch as a whole.

Pouch 1 comprises a container body 2 formed by two or more walls 4 made of flexible film, facing and joined to each other, e.g. sealed, along the edges, possibly with gusseted side walls (gusset pouch) or with a bottom wall.

According to one embodiment, the film has a single layer. Preferably, the film is multilayer.

Preferably, one or more layers of the film are made from polymers, such as e.g. polyolefins, polyamides, polyesters, polycarbonates, polymers obtained from renewable (bio-based), biodegradable, compostable sources.

Moreover, preferably one or more layers are coated with metallic oxides, e.g. aluminium oxides, silicon or combinations thereof, or with coatings, with or without metallic oxides, such as aluminium oxides.

Moreover, preferably one or more layers are impermeable to oxygen and/or to moisture and/or to light.

Moreover, preferably the film is suitable for supporting sterilisation treatments by ionising radiations, and also certain heat treatments such as pasteurization, freezing, or pressure or vacuum treatments.

Moreover, preferably the film or the single layers have a thickness between a few nanometres and a few millimetres.

Pouch 1 further comprises a spout 6 made of rigid material, sealingly applied to body 2. In particular, spout 6 typically is inserted in a section of the edge of body 2, usually between the side walls 4.

Preferably, spout 6 is made in a single piece, in plastic material, e.g. polyethylene or polypropylene, by means of injection moulding.

Spout 6 substantially extends along a longitudinal axis Z and comprises, on the side which remains inside the container body 2 of pouch 1 toward the outside, an entrance portion 8, an intermediate portion 10 and a final portion 12.

Internally, spout 6 provides a duct 14, usually cylindrical circular in shape, which extends along the longitudinal axis Z between an inlet 16 of the entrance portion 8 and an outlet 18 of the final portion 12.

The entrance portion 8 preferably is made from a pair of facing walls 20, with prevalent extension in transverse direction, i.e. perpendicular to the longitudinal axis Z, which are joined at the ends. Such walls externally form two engagement surfaces 22 intended for coupling with the films of the container body 2, preferably by means of sealing.

The final portion 12 comprises a tube 24 which extends along the longitudinal axis Z, coaxial to duct 14, typically ending with outlet 18.

According to one embodiment, the final portion 12 further comprises a thread 26 for screwing a cap 100, for example made by means of sections of interrupted thread.

Preferably, cap 100 for spout 6 comprises an outer annular wall 102 which surrounds tube 24 and for example, is provided with the thread for engaging with the thread 26 of spout 6.

Cap 100 further comprises, at one end of the outer annular wall 102, a bottom 104 suitable for closing the outlet 18 and a warranty seal 106 at the other end.

Preferably, the final portion 12 of spout 6 comprises an engagement portion suitable for engaging with the warranty seal 106 of cap 100 to create an anti-rotation restraint of said warranty seal.

In other words, cap 100 is applicable to spout 6 of the full pouch in a tamper-proof manner because the unscrewing of the cap induces the breaking of the warranty seal 106, which engages with the engagement portion of spout 6.

Moreover, according to the invention, there is provided a sacrificial closure 200 suitable for being applied to the spout 6 of the empty pouch, and in particular to the tube 24 of the final portion 12, to close outlet 18 in an irreversible manner.

In other words, the sacrificial closure 200 is irreversible because it cannot be reused or it is separable from the spout only by the cracking or breaking thereof or of tube 24 to which it is applied.

For example, the sacrificial closure 200 is formed by a thin membrane applied to the peripheral edge of outlet 18, for example by means of an adhesive or by means of soldering.

Said thin membrane can be peeled from the spout, but it cannot be reused, unless there is a new application of adhesive or after new soldering.

According to a further embodiment, the sacrificial closure 200 is formed by a septum applied to the peripheral edge of outlet 18, for example by means of an adhesive or by means of soldering. Said septum can be broken for example, by using a specific tool.

According to a further embodiment again, the sacrificial closure 200 is formed by a stopper arranged to close outlet 18, made in a single piece with said tube 24 during the moulding process.

For the opening of the spout, tube 24 is cut close to the stopper so as to move away the plugged portion.

The sacrificial closure 200 in any case makes a seal with tube 24 so as to preserve any pre-existing sterility conditions inside the pouch.

The intermediate portion 10 comprises a first support surface 30 and a second support surface 32, which substantially are lying on planes orthogonal to the longitudinal axis Z, and spaced axially.

For example, said support surfaces are formed by axially-spaced facing surfaces of a first plate 30a and a second plate 32a, respectively.

Preferably, the first plate 30a is joined to the walls 20 of the entrance portion 8, while the second plate 32a is joined to the engagement portion of the final portion 12.

Moreover, preferably the intermediate portion 10 has a first guide surface 34 and a second guide surface 36 which are parallel to each other, parallel to the longitudinal axis Z and equidistant therefrom, the guide surfaces being contained between the support surfaces 30, 32.

For example, said guide surfaces 34, 36 are formed by transversely-spaced, opposed, surfaces of guide walls 34a, 36a, respectively.

According to the invention, there is also provided a transport device 300 suitable for loading a plurality of pouches 1 provided with the respective sacrificial closure 200.

Said transport device 300 has a compartment 302 in which, when the pouch with the closure is loaded, at least a portion of spout 6 is housed and a respective sacrificial closure 200 is applied to the spout, while the possible remaining part of spout 6 and the container body 2 are arranged outside compartment 302.

Figure 2:
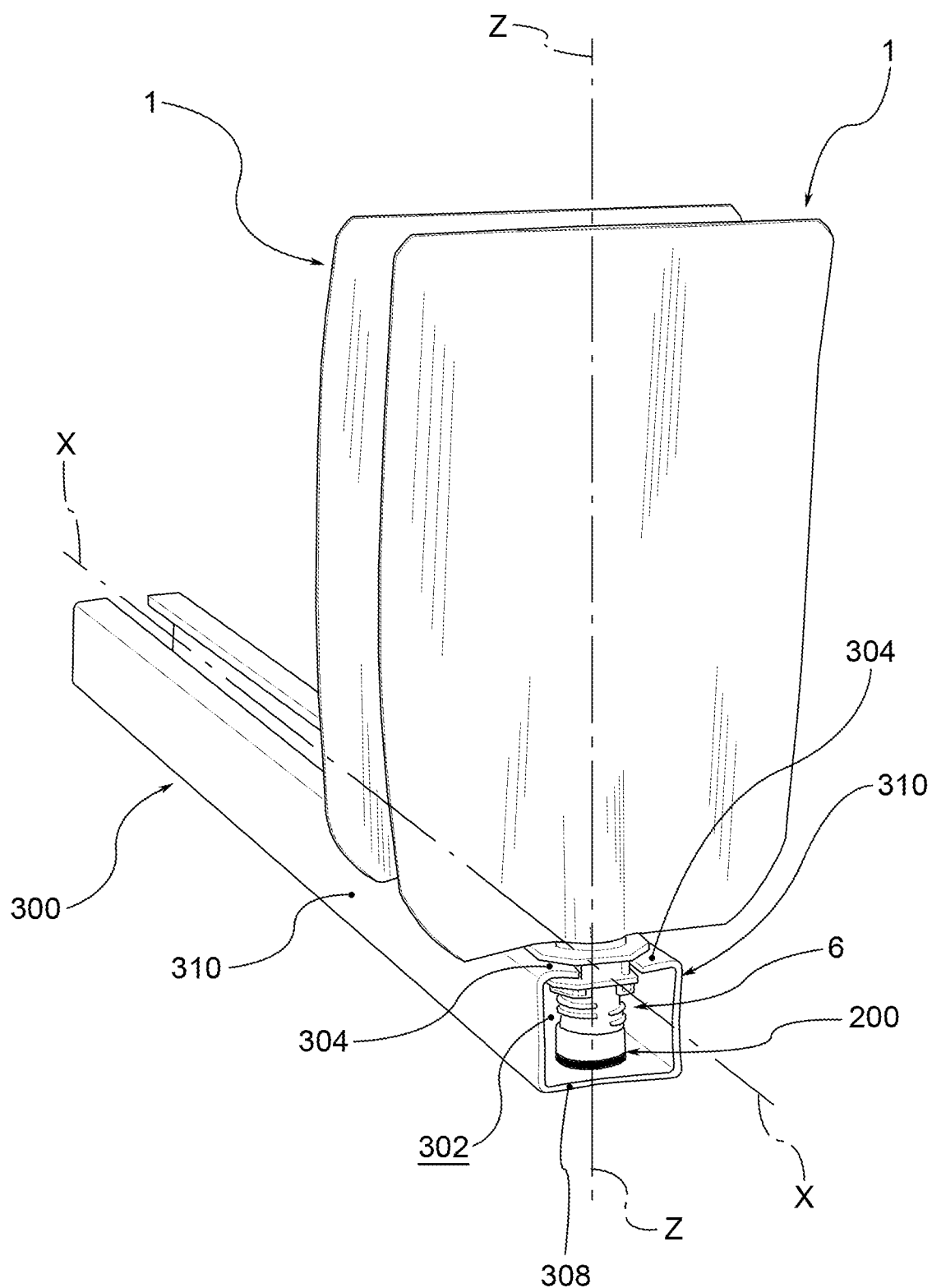
FIG. 2 shows a plurality of pouches of FIG. 1, loaded on a transport device.
Figure 3:
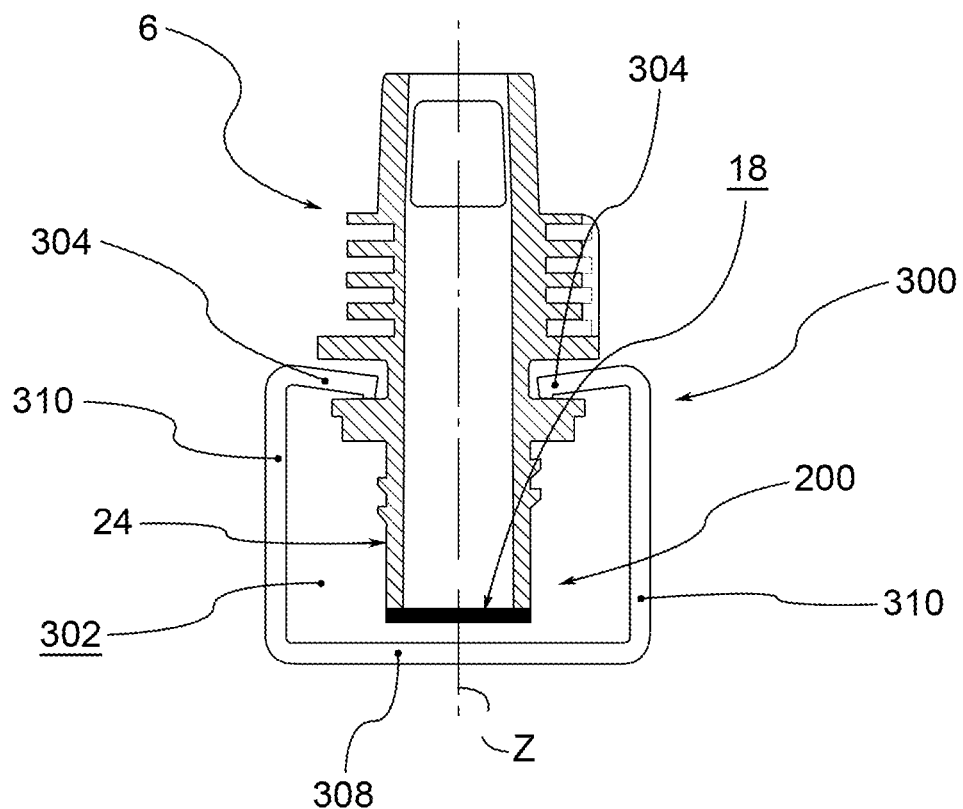
FIG. 3 depicts a sectional view of a spout provided with the sacrificial closure, partly accommodated in the transport device, made according to a first sectional plane orthogonal to an axis X in FIG. 2.
Figure 4:
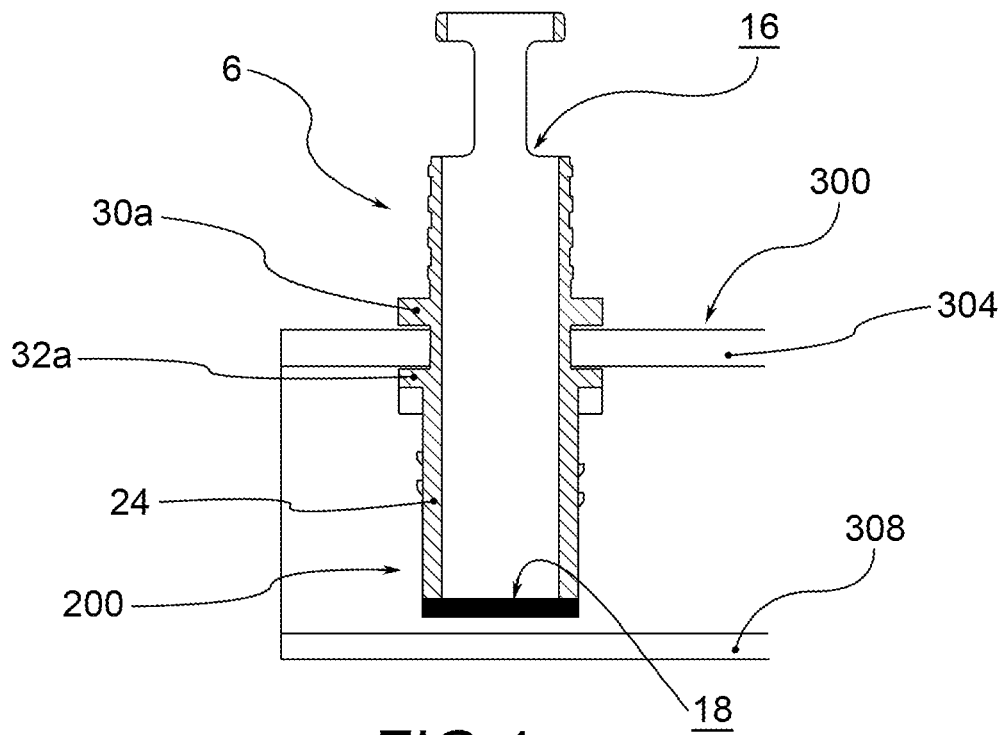
FIG. 4 shows a sectional view of the spout provided with the sacrificial closure, partly accommodated in the transport device, made according to a second sectional plane containing the axis X in FIG. 2 and orthogonal to the first sectional plane.
Figure 5:
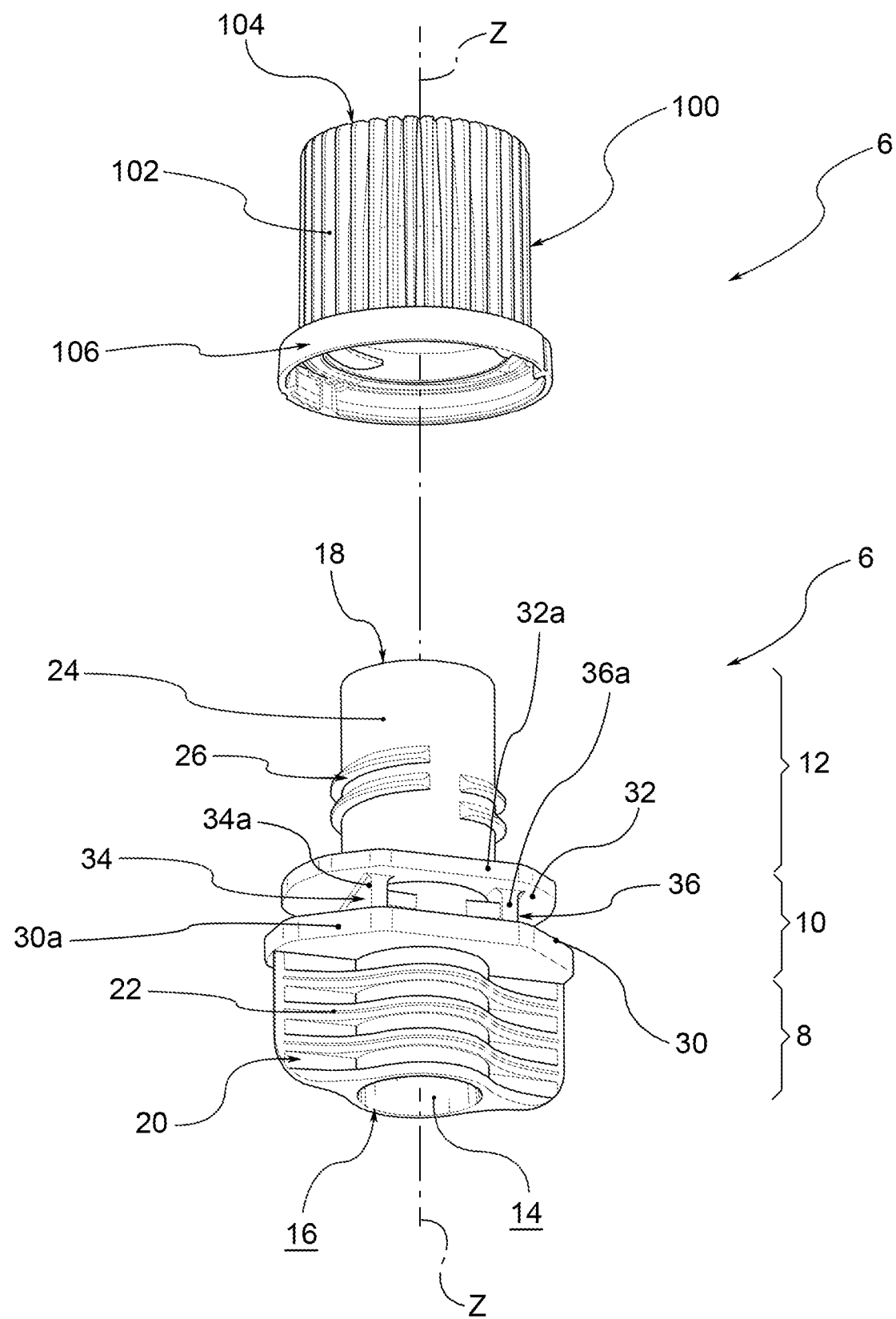
FIG. 5 shows a spout and a permanent cap applicable to the spout, in separate parts.

Moreover, the transport device 300 has support means suitable for engaging spout 6 and supporting the pouch provided with the closure, both in the "standing" configuration in which the spout is arranged at the top and the pouch at the bottom, and in the "upside down" configuration in which the spout is arranged at the bottom and the pouch at the top (FIG. 2).

Preferably, said support means comprise a pair of fins 304 suitable for being housed between the support surfaces 30, 32 of spout 6, thus creating a bilateral engagement in the direction of the longitudinal axis Z.

Moreover, said engagement means of the transport device 300 are suitable for engaging spout 6 in a sliding manner along a sliding axis X, lying on a plane orthogonal to the longitudinal axis Z.

In particular, said fins 304 allow the sliding of the pouch with the closure along the sliding axis X; preferably, said sliding is guided by the guide surfaces 34, 36 which cooperate with the fins 304.

According to a preferred embodiment, said transport device 300 comprises a section bar having extension along said sliding axis X.

Preferably, said section bar comprises a base 308 placed side-by-side side walls 310, said base covered by said fins 304, each protruding from the respective side wall 310. Base 308, the walls 310 and the fins 304 peripherally define compartment 302.

For example, with pouch 1 provided with spout 6 loaded on the section bar, the fins 304 are inserted between the support surfaces 30, 32, while the second plate 32a, tube 24 and closure 200 are contained in compartment 302.

According to the invention, a method of preparation for the sterilisation comprises a first step which provides producing a plurality of container bodies 2, the production of a plurality of spouts 6, the production (or the reuse) of a plurality of sacrificial closures 200.

Spout 6 is sealingly applied to the respective container body 2, thus obtaining a plurality of pouches 1.

In certain variant embodiments, the sacrificial closure 200 is applied to tube 24, thus making an empty provisional closed pouch to be sterilised 600.

In certain variant embodiments, the sacrificial closure 200 is integrated with the spout (stopper in a single piece with the tube), thus equally making an empty provisional closed pouch to be sterilised 600.

Moreover, the method of preparation for the sterilisation comprises a successive step of loading a plurality of transport devices 300 with empty provisional closed pouches to be sterilised, each transport device being loaded with a predetermined number of empty provisional closed pouches to be sterilised, for the collective transportation to a sterilizer.

For example, the loading step provides the insertion by sliding of the empty provisional closed pouches 600 in said section bar along said sliding axis X and the support of the provisional closed pouch, in the "standing" or "upside down" configuration, by means of the engagement of the fins 304 between the support surfaces 30, 32 of the spouts 6.

Then, preferably the method provides forming a transport group 400 containing a plurality of transport devices 300, each carrying the empty closed pouches to be sterilised, stacked.

Figure 6:
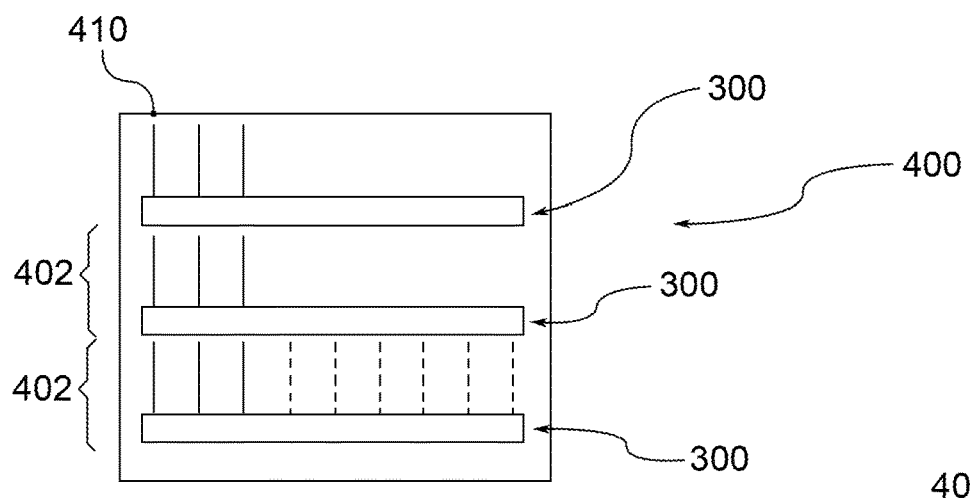
FIGS. 6 and 7 show diagrams of embodiment variants of transport groups.

According to one embodiment (FIG. 6), group 400 comprises a plurality of simple transport surfaces 402, in which each transport surface 402 comprises a predefined number of transport devices 300 placed side-by-side at the same height, all carrying the empty provisional pouches arranged in the same direction, for example all "standing", i.e. facing with the spout towards the side, or all "upside down", i.e. facing with the spout downwards. The transport surfaces 402 are stacked, thus forming the transport group 400.

Figure 7:
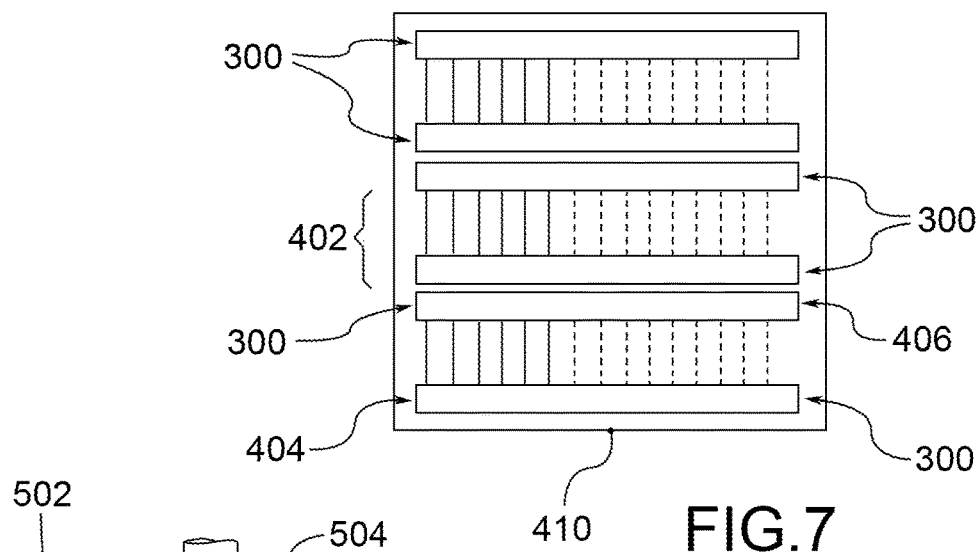
Figure 8:
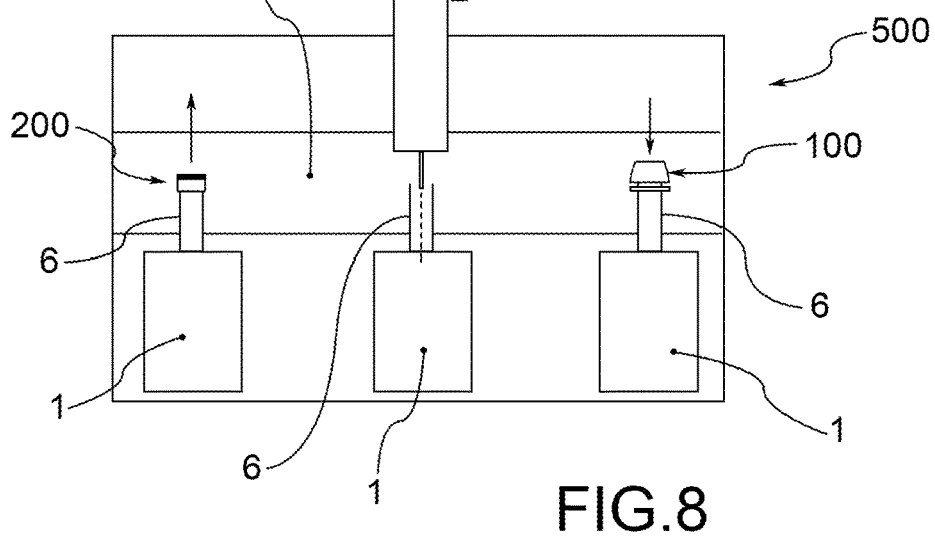
FIG. 8 depicts a diagram of a filling machine.

According to a further embodiment (FIG. 7), group 400 comprises a plurality of dual transport surfaces 402, in which each transport surface comprises a first level 404 comprising a predefined number of transport devices 300 placed side-by-side at the same height, all carrying empty provisional pouches arranged in the same direction, for example all "standing" or all "upside down", and a second level 406 superimposed on the first, comprising a predefined number of transport devices 300 placed side-by-side, all carrying the empty provisional pouches arranged in the direction opposite to that of the first level 404, for example all "upside down" or all "standing".

In the transport surfaces according to such an embodiment, the "standing" provisional pouches therefore are alternated by the "upside down" provisional pouches along the sliding axis X.

Said transport surfaces 402 also are stacked, thus forming the transport group 400.

The loading operations for forming the dual transport surfaces are shown, for pouches not provided with sacrificial closure, in European Patent EP-B1-2611704 to the Applicant, the teachings of which in this regard are incorporated herein.

Generally, the transport group 400 is housed in a box 410, e.g. a cardboard box, for transport.

The method further provides a possible transport step in which the transport group 400 is transported from the manufacturer's site to a steriliser, for example a specialized centre or a filler that also performs the sterilisation, where a sterilisation step is performed.

During the sterilisation step, the whole transport group 400, with or without box 410, or the individual simple or dual transport surfaces 402 thereof, is subjected to sterilisation by ionising radiations.

If the sterilisation step is performed at a specialized centre, the transport group 400, consisting of sterilised empty provisional closed pouches, is transported to the filler.

At the filler, the sterilised empty provisional closed pouches are picked from the transport group 400 and sent to a filling machine 500 provided with a sterile chamber 502 suitable for containing, for each sterilised empty provisional closed pouch, at least a portion of the tube 24 of spout 6 and the sacrificial closure 200 applied thereto.

The opening of the sterilised empty provisional closed pouch is performed in the sterile chamber 502 of machine 500, i.e. a step of breaking the sacrificial closure 200 or separation from the spout, so as to free the filling access.

Preferably, the sacrificial closures 200 are collected and set aside, and possibly allocated for recycling.

The filling machine 500 further comprises filling means 504 which lead into the sterile chamber 502, which are suitable for the controlled supply of the product that pouch 1 is filled with, through spout 6. Therefore a filling step is performed.

Finally, a step of applying the tamper-proof cap 100 to the tube 24 of spout 6 of the full pouch occurs in the sterile chamber 502 of machine 500.

The final, still sterile closed pouches thus obtained, provided with cap 100, leave the sterile chamber 502 and are sent to the successive packing and shipping operations.

Innovatively, the sterilisation management system according to the present invention overcomes the drawbacks of the prior art because it allows an increased number of empty pouches to be transported or handled while maintaining the sterility conditions up to the application of the final cap.

Moreover, advantageously the use of peelable membrane or of a breakable septum allows the inside of the container body to be accessed very quickly without for example, unscrewing or separating a sacrificial closure applied by pressure or screwing.

According to a further advantageous aspect, the use of a stopper in a single piece with the tube of the spout avoids the step of applying a sacrificial closure by pressure or screwing, since the stopper is made directly during the moulding step of the spout.

It is apparent that those skilled in the art may make modifications to the above-described method and device in order to meet contingent needs, without departing from the scope of protection defined by the claims.

The invention claimed is:

1. A method of preparation for sterilization of empty pouches, comprising the steps of:
   producing a plurality of pouches at a manufacturer's site, wherein each pouch comprises a container body formed by walls made of flexible film and a spout comprising an entrance portion with an inlet and a tube with an outlet, said spout being sealingly applied to the container body so as to protrude outside of the container body with at least a section of the tube;
   providing said spout of the empty pouch with an irreversible sacrificial closure, formed by a peelable membrane or a breakable septum, for the outlet of the spout, thereby obtaining empty provisional closed pouches to be sterilized;
   loading a plurality of empty provisional closed pouches to be sterilized on a transport device for collective transportation to a sterilizer;
   forming a stacked transport group containing a plurality of transport devices, stacked;
   transporting the transport group from the manufacturer's site towards the sterilizer in the form of a specialized center or a filler that also performs a sterilization by ionizing radiation, where a sterilization step is to be performed; and
   performing the sterilization on the whole transport group by ionizing radiation on the transport group, thereby obtaining sterilized empty closed pouches,
   wherein the transport device consists of a section bar having prevalent extension along a sliding axis and the loading step involves insertion by sliding of the empty provisional closed pouches in said section bar along said sliding axis;
   wherein the spout further comprises first and second support surfaces,
   wherein the transport device is provided with fins suitable to support the pouch by engaging the fins between the first and second support surfaces of the spout;

wherein the pouches are slidable in the section bar along said sliding axis;

wherein the fins of the transport device cooperate with first and second guide surfaces of the spout to guide the sliding of the pouch in the section bar, the fins suitable for engaging the spout between the first and second guide surfaces and supporting the pouch in both a "standing" configuration where the spout is arranged at the top and the pouch at the bottom and in an "upside down" configuration where the spout is arranged at the bottom and pouch at the top;

wherein the first and second guide surfaces are flat and parallel to each other, parallel to a longitudinal axis of the pouch, and equidistant from the longitudinal axis, the first and second guide surfaces being contained between the first and second support surfaces; and wherein said guide surfaces are formed by transversely-spaced, opposed, surfaces of first and second guide walls, respectively.

2. The method according to claim 1, wherein the loading step provides for support of the provisional closed pouch, in a "standing" configuration or an "upside down" configuration through the use of the fins between the first and second support surfaces of the spouts.

3. The method according to claim 1, wherein after the step of loading the empty provisional closed pouches to be sterilized on the transport device, there is provided the step of forming a transport group containing a plurality of stacked transport devices.

4. A method of sterilization of empty flexible pouches, comprising the steps of:

providing a transport group comprising a plurality of transport devices, each carrying empty closed pouches to be sterilized, said transport devices stacked, wherein each empty closed pouch to be sterilized comprises a container body having walls made of film, a spout sealingly applied to the container body, and a sacrificial closure, formed by a peelable membrane or a breakable septum, sealingly and irreversibly engaged to an inlet of a tube of the spout to close the spout; and performing a sterilization on the whole transport group by ionizing radiation;

wherein the transport device consists of a section bar having prevalent extension along a sliding axis and the providing step involves insertion by sliding of the empty provisional closed pouches in said section bar along said sliding axis;

wherein the spout further comprises first and second support surfaces, wherein the transport device is provided with fins suitable to support the pouch by engaging the fins between the first and second support surfaces of the spout;

wherein the pouches are slidable in the section bar along said sliding axis;

wherein the fins of the transport device cooperate with first and second guide surfaces of the spout to guide the sliding of the pouch in the section bar, the fins suitable for engaging the spout between the first and second guide surfaces and supporting the pouch in both a "standing" configuration where the spout is arranged at the top and the pouch at the bottom and in an "upside down" configuration where the spout is arranged at the bottom and pouch at the top;

wherein the first and second guide surfaces are flat and parallel to each other, parallel to a longitudinal axis of the pouch, and equidistant from the longitudinal axis, the first and second guide surfaces being contained between the first and second support surfaces; and wherein said guide surfaces are formed by transversely-spaced, opposed, surfaces of first and second guide walls, respectively.

5. A method for filling flexible pouches, comprising the steps of:

providing a transport group comprising a plurality of transport devices, each carrying sterilized empty closed pouches, said transport devices stacked, wherein each sterilized empty closed pouch comprises a container body having walls made of film, a spout sealingly applied to the container body, and a sacrificial closure, formed by a peelable membrane or a breakable septum, sealingly and irreversibly engaged to an inlet of a tube of the spout to close the spout;

picking the sterilized empty closed pouches from the transport group and sending them in succession to a sterile chamber;

for each sterilized empty closed pouch, making at least a portion of the tube provided with the sacrificial closure to pass through the sterile chamber; and during said passing through the sterile chamber, opening the spout, filling the sterilized open pouch and applying a tamper-proof cap to the tube to close the pouch;

wherein the transport device consists of a section bar having prevalent extension along a sliding axis and the providing step involves insertion by sliding of the empty provisional closed pouches in said section bar along said sliding axis;

wherein the spout further comprises first and second support surfaces, wherein the transport device is provided with fins suitable to support the pouch by engaging the fins between the first and second support surfaces of the spout;

wherein the pouches are slidable in the section bar along said sliding axis;

wherein the fins of the transport device cooperate with first and second guide surfaces of the spout to guide the sliding of the pouch in the section bar, the fins suitable for engaging the spout between the first and second guide surfaces and supporting the pouch in both a "standing" configuration where the spout is arranged at the top and the pouch at the bottom and in an "upside down" configuration where the spout is arranged at the bottom and pouch at the top;

wherein the first and second guide surfaces are flat and parallel to each other, parallel to a longitudinal axis of the pouch, and equidistant from the longitudinal axis, the first and second guide surfaces being contained between the first and second support surfaces; and wherein said guide surfaces are formed by transversely-spaced, opposed, surfaces of first and second guide walls, respectively.

6. A method of sterilization of empty flexible pouches, comprising the steps of:

producing a plurality of pouches, wherein each pouch comprises a container body formed by walls made of flexible film and a spout comprising an entrance portion with an inlet and a tube with an outlet, said spout being sealingly applied to the container body so as to protrude outside of the container body with at least a section of the tube;

providing said spout of the empty pouch with an irreversible sacrificial closure, formed by a peelable membrane or a breakable septum, for the outlet of the spout, thereby obtaining empty provisional closed pouches to be sterilized;

loading a plurality of empty provisional closed pouches to be sterilized on a transport device for collective transportation;

performing a sterilization of the transport device loaded with empty provisional closed pouches, by ionizing radiation;

picking the sterilized empty provisional closed pouches from the transport device and sending them in succession to a sterile chamber;

for each sterilized empty closed pouch, making at least a portion of the tube provided with the sacrificial closure to pass through the sterile chamber; and during said passing through the sterile chamber, opening the spout, filling the sterilized open pouch and applying a tamper-proof cap to the tube to close the pouch;

wherein the transport device consists of a section bar having prevalent extension along a sliding axis and the loading step involves insertion by sliding of the empty provisional closed pouches in said section bar along said sliding axis;

wherein the spout further comprises first and second support surfaces, wherein the transport device is provided with fins suitable to support the pouch by engaging the fins between the first and second support surfaces of the spout;

wherein the pouches are slidable in the section bar along said sliding axis;

wherein the fins of the transport device cooperate with first and second guide surfaces of the spout to guide the sliding of the pouch in the section bar, the fins suitable for engaging the spout between the first and second guide surfaces and supporting the pouch in both a "standing" configuration where the spout is arranged at the top and the pouch at the bottom and in an "upside down" configuration where the spout is arranged at the bottom and pouch at the top;

wherein the first and second guide surfaces are flat and parallel to each other, parallel to a longitudinal axis of the pouch, and equidistant from the longitudinal axis, the first and second guide surfaces being contained between the first and second support surfaces; and wherein said guide surfaces are formed by transversely-spaced, opposed, surfaces of first and second guide walls, respectively.

7. An assembly comprising:
a transport device for collective transportation of empty flexible pouches; and
a plurality of empty provisional closed pouches to be sterilized loaded on the transport device, wherein each empty provisional closed pouch to be sterilized comprises a container body having walls made of film, a spout sealingly applied to the container body, and a sacrificial closure, formed by a peelable membrane or a breakable septum, sealingly and irreversibly engaged to an inlet of a tube of the spout to close the spout, wherein the spout further comprises first and second support surfaces, wherein the transport device is provided with fins suitable to support the pouch by engaging the fins between the first and second support surfaces of the spout, wherein the transport device is a section bar having prevalent extension along a sliding axis, wherein the pouches are slidable in the section bar along said sliding axis, wherein the fins of the transport device cooperate with first and second guide surfaces of the spout to guide the sliding of the pouch in the section bar, the fins suitable for engaging the spout between the first and second guide surfaces and supporting the pouch in both a "standing" configuration where the spout is arranged at the top and the pouch at the bottom and in an "upside down" configuration where the spout is arranged at the bottom and pouch at the top;

wherein the first and second guide surfaces are flat and parallel to each other, parallel to a longitudinal axis of the pouch, and equidistant from the longitudinal axis, the first and second guide surfaces being contained between the first and second support surfaces; and wherein said guide surfaces are formed by transversely-spaced, opposed, surfaces of first and second guide walls, respectively.

8. An assembly according to claim 7, wherein the section bar has a compartment delimited in part by a base, said compartment being suitable to accommodate at least a portion of the tube of the spout and the sacrificial closure engaged with said tube.

9. A transport group comprising a plurality of simple transport surfaces, wherein each transport surface comprises a predefined number of assemblies according to claim 8, placed side-by-side at the same height and carrying provisional closed pouches to be sterilized arranged in the same direction, wherein the provisional closed pouches to be sterilized are all "standing" or all "upside down", and wherein the transport surfaces are stacked.

10. A transport group comprising a plurality of dual transport surfaces, wherein each transport surface comprises:
a first level comprising a predefined number of assemblies according to claim 8, placed side-by-side at the same height, all carrying empty provisional closed pouches to be sterilized arranged in the same direction, wherein the provisional closed pouches to be sterilized are all "standing" or all "upside down", and
a second level superimposed on the first, comprising a predefined number of assemblies according to claim 8, placed sides-by-side and carrying the empty provisional closed pouches to be sterilized arranged in a direction opposite to that of the first level, wherein the provisional closed pouches to be sterilized are all "upside down" or all "standing",
and wherein said transport surfaces are stacked.

11. A transport group comprising a plurality of simple transport surfaces, wherein each transport surface comprises a predefined number of assemblies according to claim 7, placed side-by-side at the same height and carrying provisional closed pouches to be sterilized arranged in the same direction, wherein the provisional closed pouches to be sterilized are all "standing" or all "upside down", and wherein the transport surfaces are stacked.

12. A transport group comprising a plurality of dual transport surfaces, wherein each transport surface comprises:
a first level comprising a predefined number of assemblies according to claim 7, placed side-by-side at the same height, all carrying empty provisional closed pouches to be sterilized arranged in the same direction, wherein the provisional closed pouches to be sterilized are all "standing" or all "upside down", and
a second level superimposed on the first, comprising a predefined number of assemblies according to claim 7, placed side-by-side and carrying the empty provisional closed pouches to be sterilized arranged in a direction opposite to that of the first level, wherein the provisional closed pouches to be sterilized are all "upside down" or all "standing", and
wherein said transport surfaces are stacked.

* * * * *